United States Patent

Wakasugi et al.

[11] Patent Number: 5,416,226
[45] Date of Patent: May 16, 1995

[54] PROCESS FOR THE MANUFACTURE OF TRIMERS OF ALIPHATIC ALDEHYDE WITH CHLORINATED 2-POSITION

[75] Inventors: Takashi Wakasugi; Tadashi Miyakawa; Naka Tonouchi; Fukuichi Suzuki; Takashi Yamauchi, all of Fukushima, Japan

[73] Assignee: Kureha Chemical Industry Co., Ltd., Tokyo, Japan

[21] Appl. No.: 97,755

[22] Filed: Jul. 26, 1993

[30] Foreign Application Priority Data

Apr. 21, 1993 [JP] Japan .................................. 5-117810

[51] Int. Cl.$^6$ ............................................. C07D 323/06
[52] U.S. Cl. ................................................. 549/368
[58] Field of Search ............................ 549/368, 367

[56] References Cited

U.S. PATENT DOCUMENTS

| | | | |
|---|---|---|---|
| 3,697,546 | 10/1972 | Asakawa et al. | 549/368 |
| 4,332,644 | 6/1982 | Hamanaka et al. | 549/368 |
| 4,720,557 | 1/1988 | Erdman | 549/368 |
| 5,008,462 | 4/1991 | Ishizuk et al. | 568/466 |
| 5,196,552 | 3/1993 | Senaratne et al. | 549/396 |
| 5,274,131 | 12/1993 | Wakasugi et al. | 549/368 |

OTHER PUBLICATIONS

Chemical Abstracts, vol. 89, #646896, Tsushiya et al., 1978, "Treatment of chloroaldehyde-containing waste waters".

Primary Examiner—C. Warren Ivy
Assistant Examiner—Raymond Covington
Attorney, Agent, or Firm—Burgess, Ryan & Wayne

[57] ABSTRACT

A process for manufacturing a trimer of a low aliphatic aldehyde having 2–5 carbon atoms and the chlorinated 2-position is disclosed. The process comprises cyclically trimerizing said aliphatic aldehyde with chlorinated 2-position in the presence of a catalyst selected from the group consisting of metallic tin, metallic zinc, zeolite, and Lewis acids. It ensures easy separation of the catalyst from the target trimer and a high yield of the trimer. In addition, the unreacted raw material can be easily recovered.

10 Claims, No Drawings

PROCESS FOR THE MANUFACTURE OF TRIMERS OF ALIPHATIC ALDEHYDE WITH CHLORINATED 2-POSITION

BACKGROUND OF THE INVENTION

1. Field of the Invention

The present invention relates to a process for the manufacture of a trimer of an aliphatic aldehyde with a chlorinated 2-position.

2. Description of the Background Art

Monochloroacetaldehyde (hereinafter abbreviated to MCA), 2-chloropropionaldehyde (hereinafter abbreviated to CPA), 2-chlorobutyraldehyde (hereinafter abbreviated to CBA), and the like are known as aliphatic aldehydes with a chlorinated 2-position (hereinafter called 2-chloroaldehydes). These 2-chloroaldehydes are useful compounds as raw materials for the synthesis of organic compounds such as drugs, agrichemicals, and the like.

However, these 2-chloroaldehydes are unstable because of their possession of two functional groups; i.e., a high activity chlorine atom and an aldehyde group, in one molecule. Thus, it is difficult to stably store them for a long period of time. Technology for storing 2-chloroaldehyde in a stable manner for a long period of time is therefore desired.

In order to solve this problem, U.S. Pat. No. 5,008,462, for example, discloses that MCA can be stored as the trimer in a stable manner by the cyclic trimerization of MCA and that the trimer is easily regenerated into high purity MCA. This U.S. patent also discloses a process for manufacturing the MCA trimer.

According to the process for manufacturing the MCA trimer disclosed by U.S. Pat. No. 5,008,462, a chlorinated acetaldehyde solution containing MCA as a major component is dissolved into an organic solvent and reacted in the presence of concentrated sulfuric acid to produce MCA trimer. The same organic solvent and water are then added to the reaction mixture, in which part of the MCA trimer is present as crystals, in order to dissolve the crystals into the organic solvent and to separate a aqueous layer containing sulfuric acid. The organic layer is washed with water and the MCA trimer is recrystallized from the organic layer for separation.

Regarding the manufacture of CPA trimer, EP 0484 742 A1 discloses a method of trimerizing CPA by adding concentrated sulfuric acid to a mixture of a solution of chlorinated propionaldehyde and an organic solvent in the same manner as in the case of MCA.

These processes for the manufacture of MCA trimer or CPA trimer, in which the trimerization of 2-chloroaldehyde is carried out in the presence of concentrated sulfuric acid, however, involves difficulty in separating the produced trimer from concentrated sulfuric acid. Washing of the organic layer containing the trimer is required for the removal of concentrated sulfuric acid. Since unreacted 2-chloroaldehyde is easily soluble in water, not only the recovery of 2-chloroaldehyde is difficult, but also there are problems in the treatment of the waste water.

SUMMARY OF THE INVENTION

An object of the present invention is to provide a process for the manufacture of a 2-chloroaldehyde trimer represented by the following formula,

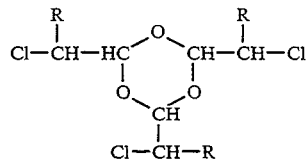

wherein R represents a hydrogen atom, a methyl group, an ethyl group, or a propyl group, in which the separation of the target product and the trimerization catalyst is easy and which gives a high yield.

Another object of the present invention is to provide a process for the manufacture of 2-chloroaldehyde trimer, by which the unreacted 2-chloroaldehyde can be easily recovered.

Still another object of the present invention is to provide a process for the manufacture of 2-chloroaldehyde trimer, in which there are no problems in the disposal of waste water.

These objects are solved according to the present invention by the provision of a process for the manufacture of a trimer of 2-chloroaldehyde which comprises cyclically trimerizing the 2-chloroaldehyde in the presence of a catalyst selected from the group consisting of metallic tin, metallic zinc, zeolite, and Lewis acids.

The above objects are further solved according to the present invention by the provision of a process for manufacturing a trimer of a lower aliphatic aldehyde with chlorinated 2-position comprising, a step of chlorinating an aliphatic aldehyde having 2 to 5 carbon atoms to produce a chlorinated solution containing the aliphatic aldehyde with chlorinated 2-position, a step of distilling said chlorinated solution to remove unreacted aldehyde and high-boiling components, a step of cyclically trimerizing said aliphatic aldehyde with chlorinated 2-position by the addition of a catalyst selected from the group consisting of metallic tin, metallic zinc, zeolite, and Lewis acids, and a step of separating all or a major portion of said catalyst and the organic solvent from the reaction mixture obtained by the cyclic trimerization reaction and separating the trimer of the aliphatic aldehyde with chlorinated 2-position as crystals.

Other objects, features and advantages of the invention will hereinafter become more readily apparent from the following description.

DETAILED DESCRIPTION OF THE INVENTION AND PREFERRED EMBODIMENTS

2-Chloroaldehyde which is a raw material for the manufacture of a trimer of the present invention is a $C_2$–$C_5$ aliphatic aldehyde with chlorinated 2-position such as, MCA, CPA, CBA, or the like. MCA, CPA, and CBA can be obtained by chlorinating the corresponding aldehyde, i.e, acetaldehyde (or para-aldehyde), propionaldehyde, or butyraldehyde.

In order to efficiently obtain 2-chloroaldehyde while suppressing the side production of dichloroaldehyde, the chlorination reaction of the corresponding aldehyde for the manufacture of the 2-chloroaldehyde is desirably carried out by terminating the reaction at a degree of the chlorination (the average number of chlorine atoms bonded to one molecule of aldehyde) in the range of 0.5 to 1.2. The chlorinated aldehyde solution thus obtained contains, beside 2-chloroaldehyde, the unreacted raw material, dichloroaldehyde of which the side production cannot be avoided, and high-boiling components.

For the trimerization of 2-chloroaldehyde, it is desirable to prepare a solution containing 70% or more of 2-chloroaldehyde by removing the unreacted raw material, high-boiling components, and the like from said chlorinated aldehyde solution by distillation. Atmospheric distillation, vacuum distillation, or azeotropic distillation may be used for the distillation, with the azeotropic distillation being preferred. The azeotropic distillation is particularly useful for easily producing a chlorinated solution with a purity of 2-chloroaldehyde concentration (the purity excluding the azeotropic solvent) of 90% or higher. Aromatic hydrocarbons (e.g., benzene), aliphatic hydrocarbons (e.g., hexane), alicyclic hydrocarbons (e.g., cyclohexane), chloroform, and the like are given as examples of solvents which can be azeotropically distilled with the 2-chloroaldehyde.

The trimerization reaction can be carried out by reacting the 2-chloroaldehyde, which contained in the chlorinated solution obtained by the distillation or a solution obtained by diluting such a chlorinated solution with a solvent, in the presence of metallic tin, metallic zinc, zeolite, or a Lewis acid, as a catalyst.

The metallic tin and metallic zinc of any form which can ensure smooth stirring and separation thereof after the reaction can be used as the trimerization catalyst, with particles having a diameter about 1 to 10 mm being preferred. Y-type zeolite, L-type zeolite, mordenite, and the like are given as examples of zeolite used as the catalyst. As Lewis acids, stannous chloride, zinc chloride, antimony trichloride, and the like are exemplified.

The amount of the catalyst varies depending on the type of the catalyst used, the kind of 2-chloroaldehyde, the concentration of the 2-chloroaldehyde in the solution, the reaction temperature, and other conditions of the reaction (e.g., whether the reaction is carried out with stirring). When metallic tin particles or metallic zinc particles having a diameter of about 1 to 10 mm are used as the catalyst, an amount of such metallic tin particles or zinc particles in the range of 1–15%, preferably 2–12%, of the amount of 2-chloroaldehyde is used. Optionally, a reaction vessel or a stirrer of which the surfaces are coated with tin or zinc may be used instead of the metal particles. In the case of zeolite, an amount in the range of 50–250%, preferably 80–220%, of the amount of 2-chloroaldehyde can be used. Lewis acid catalysts can be used in an amount of 0.1–10%, and preferably 0.3–8%.

Aliphatic hydrocarbons having 5–10 carbon atoms, such as hexane, heptane, or the like; alicyclic hydrocarbons such as cyclohexane or the like; aromatic hydrocarbons such as benzene, toluene, xylene, or the like; chloral, carbon disulfide, and the like are given as examples of organic solvents used for the dilution of the chlorinated solution. These organic solvents can be used in an amount of 0.5 to 10 times, preferably 0.8 to 5 times, in volume of the amount of the raw material chlorinated solution.

The reaction temperature is above the temperature at which the reaction solution does not solidify and below 50° C., preferably between 0° and 45° C. If the reaction temperature is higher than 50° C., the production of high boiling point components increases; if it is lower than 0° C., the reaction is retarded.

The reaction catalyst is removed after the completion of the reaction. When metallic tin, metallic zinc, or zeolite, which is present as the solid in the reaction mixture, is used as the catalyst, the catalyst is removed by filtration or decantation.

Some of lewis acid catalysts may form an oily layer in the reaction solution. In such a case, the catalyst layer is removed by decantation. The reaction solution from which the catalyst has been removed is submitted to distillation, preferably to vacuum distillation, to remove the unreacted 2-chloroaldehyde and all or a major portion of the solvent. In the case where the catalyst is dissolved in the reaction solution, the reaction solution is distilled as is to remove the unreacted 2-chloroaldehyde and all or a major portion of the solvent, followed by separation of the catalyst by washing the residual liquid with water.

The target trimer is precipitated as the trimerization reaction proceeds in the case where the reaction is carried out in the absence of a solvent, and even in the case where the reaction is carried out using a solvent depending on the kind and the amount of the solvent used. When the crystals are precipitated, the catalyst, unreacted raw material, and high-boiling components are separated in the same manner as mentioned above after the reaction mixture is heated to dissolve the crystals.

When the reaction liquid from which the catalyst, unreacted raw material, and high-boiling components have been separated in this manner is allowed to stand still at a temperature below room temperature, preferably at 0° to 15° C., crystals of the target trimer are precipitated. The target trimer having a purity of 99% or more can be obtained by recrystallizing the crystals thus produced in methanol or the like. In the case of CBA trimer, the product in the state of a viscous liquid before crystallization may be submitted to such a recrystallization procedure, because the crystallization of CBA trimer takes a long period of time.

The 2-chloroaldehyde trimers thus obtained can be stored stably at room temperatures for a long period of time. These trimers can be subjected to reactions as are. They can be depolymerized into 2-chloroaldehyde of high purity, when heated and distilled in the presence of an acid catalyst.

Other features of the invention will become apparent in the course of the following description of the exemplary embodiments which are given for illustration of the invention and are not intended to be limiting thereof.

EXAMPLES

Example 1

Synthesis of MCA Trimer (Preparation of MCA)

Into a 500 ml three-necked flask equipped with a stirrer, a condenser, and a thermometer were charged 140 g of para-aldehyde and 1.4 ml of water. Chlorine gas was introduced into this solution maintained at 10° C. at a rate of 200 ml/min to initiate the chlorination reaction. Then, while maintaining the temperature of the solution at 6°±3° C., chlorine gas was introduced at a rate of 200 to 700 ml/min for 8.5 hours, thus obtaining 300 g of a chlorinated solution. At this time, a generated hydrogen chloride gas was absorbed in an aqueous solution of sodium hydroxide.

The chlorinated solution was submitted to atmospheric distillation to remove low-boiling components such as the unreacted acetaldehyde and the like, followed by azeotropic distillation while adding 260 g of benzene at a rate of 20 g/min, thus obtaining 420 g of a distillate which distilled at 60° to 68° C. This distillate was confirmed to contain 32% of MCA, 58% of benzene, and 2% of acetaldehyde by gas chromatography. The yield of MCA recovered in the distillate was 90% of the MCA in the chlorinated solution.

(Synthesis of Trimer)

A 500 ml three-necked flask equipped with a stirrer and a thermometer was used for the synthesis of MCA trimer. 420 g of the distillate having the above composition was reacted in the presence of 6.7 g of metallic tin (5% of MCA) at 20° C. for 3 hours. After the completion of the reaction, the metallic tin was recovered by filtration and the filtrate was distilled under vacuum to evaporate benzene and the unreacted aldehyde, thus obtaining 104 g of white crystals of MCA trimer. The purity of the MCA trimer thus produced was 98.5% and the yield was 76% of the MCA present in the distillate used for the trimerization reaction. The crystals were recrystallized from methanol to obtain 88 g of white crystals of MCA trimer having a purity of 99.5%. The metallic tin was recovered with no reduction in the weight and could be recycled to the reaction without subjecting it to the activating treatment.

Example 2

Synthesis of CPA Trimer (Preparation of CPA)

Propionaldehyde in an amount of 150 g was charged into a 500 ml three-necked flask equipped with a stirrer, a condenser, and a thermometer, and maintained at 5° C. Chlorine gas was introduced at a rate of 100 ml/min to initiate the chlorination reaction. Then, while maintaining the temperature at 5°±1° C., chlorine gas was introduced at a rate of 200 to 800 ml/min, thus obtaining 220 g of a chlorinated solution. At this time, a generated hydrogen chloride gas was absorbed in an aqueous solution of sodium hydroxide.

Azeotropic distillation was carried out on the mixture of 220 g of the chlorinated solution and 200 g of benzene to obtain 340 g of a distillate which distilled at 72° to 82° C. This distillate was confirmed by gas chromatography analysis to contain 37% of CPA, 56% of benzene, and high-boiling components. The amount of CPA distilled was 85% of the CPA contained in the chlorinated solution.

(Synthesis of Trimer)

A 500 ml three-necked flask equipped with a stirrer and a thermometer was used for the synthesis of CPA trimer. 340 g of the distillate having the above composition was reacted in the presence of 12.6 g of metallic tin (10% of CPA) at 20° C. for 3 hours. After the completion of the reaction, the metallic tin was separated by filtration and the filtrate was distilled under vacuum to evaporate benzene and the unreacted aldehyde, thus obtaining 82 g of white crystals of CPA trimer. The purity of the CPA trimer thus produced was 99.0% and the yield based on the CPA contained in the distillate used for the trimerization reaction was 65%.

The metallic tin could be recycled to the reaction without subjecting it to the activating treatment. The benzene and unreacted aldehyde recovered by the vacuum evaporation were also able to be recycled for reuse in the reaction.

Example 3

Synthesis of MCA Trimer

MCA trimer was synthesized by using metallic zinc as the catalyst instead of the metallic tin trimerization catalyst used in Example 1.

A solution containing 30% MCA which was obtained in the same manner as in Example 1 was used for the trimerization reaction. To 350 g of this solution was added 10.5 g of metallic zinc (10% of MCA), and the mixture was reacted at 20° C. for 3 hours. After the completion of the reaction, the metallic zinc was recovered by filtration and the filtrate was distilled under vacuum to evaporate benzene and the unreacted aldehyde, thus obtaining 81 g of white crystals of MCA trimer. The purity of the MCA trimer thus produced was 98.5% and the yield based on the MCA contained in the distillate used for the trimerization reaction was 76%. The crystals were recrystallized from methanol to obtain 66 g of white crystals of MCA trimer having a purity of 99.5%. The metallic zinc was recovered with only a slight reduction in the weight and could be recycled to the reaction without subjecting it to the activating treatment.

Example 4

Synthesis of MCA Trimer (Preparation of MCA)

Into a 2 l three-necked flask equipped with a stirrer, a condenser, and a thermometer were charged 500 g of para-aldehyde and 5 ml of water. Chlorine gas was introduced into this solution maintained at 10° C. at a rate of 150 ml/min to initiate the chlorination reaction. Then, while maintaining the temperature at 2°±1° C., chlorine gas was introduced in a total amount of 12.1 mol at a rate of 150 to 800 ml/min, thus obtaining a chlorinated solution containing MCA.

At this time, a generated hydrogen chloride gas was absorbed in an aqueous solution of sodium hydroxide.

The chlorinated solution was submitted to atmospheric distillation to remove low-boiling point components such as the unreacted acetaldehyde and the like, to obtain 860 g of a chlorinated solution containing MCA as a major component. This chlorinated solution was submitted to azeotropic distillation while adding 750 g of benzene at a rate of 60 g/min.

A distillate which distilled at 60° to 68° C. of an amount of 1,195 g was thus obtained. This distillate was confirmed to contain 32.5% of MCA, 58.2% of benzene, and 3.4% of acetaldehyde by gas chromatography. The yield of MCA recovered in the distillate was 91% of the MCA in the chlorinated solution.

(Synthesis of Trimer)

A 2 l three-necked flask equipped with a stirrer and a thermometer was used foe the synthesis of MCA trimer. 1,000 g of the distillate obtained by the azeotropic distillation and having the above composition was reacted in the presence of 5 g of zinc chloride at 30° C. for 5 hours while stirring. After the completion of the reaction, the zinc chloride catalyst forming an oily layer was separated by decantation. The residue was distilled under vacuum to evaporate benzene and the unreacted aldehyde, thus obtaining crystals. The crystals were recrystallized from methanol to obtain 246 g of white crystals of MCA trimer having a purity of 99.5%. The yield of the MCA trimer based on the MCA contained in the distillate used for the trimerization reaction was 75%.

The recovered benzene and unreacted aldehyde not trimerized could be recycled for reuse in the reaction.

Example 5

Synthesis of MCA Trimer (Preparation of MCA)

A chlorinated para-aldehyde reaction solution was prepared in the same manner as in Example 4. This reaction solution was submitted to vacuum distillation, in place of the azeotropic distillation in Example 1, to obtain a chlorinated solution containing MCA as a major component and having a boiling point range of 60° to 80° C. at 20.0 to 26.6 kPa. Gas chromatography analysis confirmed that this chlorinated solution contained 84.5% of MCA, 6.5% of dichloroacetaldehyde, and high-boiling components.

(Synthesis of Trimer)

Using the same equipment as used in Example 4, 200 g of the distillate obtained by the vacuum distillation was dissolved into 500 g of benzene. After the addition of 350 g of H-mordenite (HSZ-620HOA: trademark, manufactured by Tosoh Co., Ltd.), the trimerization reaction was carried out at 30° C. for 5 days while stirring. After the completion of the reaction, H-mordenite catalyst was removed by filtration and the filtrate was distilled under vacuum to evaporate benzene and the unreacted aldehyde, thus obtaining crystals. The crystals were recrystallized from hexane to obtain 128 g of white crystals of MCA trimer having a purity of 99.2%.

The yield of the MCA trimer based on the MCA contained in the distillate used for the trimerization reaction was 75%.

Comparative Example

Synthesis of MCA Trimer (Preparation of MCA)

A chlorinated solution prepared in the same manner as in Example 4 was subjected to the trimerization reaction using sulfuric acid as the catalyst.

(Synthesis of Trimer)

Using the same equipment as used in Example 4, 1,000 g of the distillate obtained by the azeotropic distillation was reacted to trimerize with the addition of 10 g of 96% sulfuric acid at 0° C. for 5 hours while stirring. After the completion of the reaction, the water layer was separated and the organic layer was washed with water and 10% aqueous solution of sodium hydroxide. The organic layer was then dried over magnesium sulfate and distilled under vacuum to evaporate benzene, thus obtaining crystals. The crystals were recrystallized from methanol to obtain 171 g of white crystals of MCA trimer having a purity of 99.5%. The yield of the MCA trimer based on the MCA contained in the distillate used for the trimerization reaction was 52.4%.

It was difficult to recover MCA not trimerized, because MCA was dissolved into the aqueous layer and the water used for the washing.

Example 6

Synthesis of CBA Trimer (Preparation of CBA)

Into a 2,000 ml three-necked flask equipped with a stirrer, a condenser, and a thermometer were charged 500 g of butyraldehyde and 5 ml of water, and the mixture was maintained at 5° C. Chlorine gas was introduced into this solution at a rate of 100 ml/min to initiate the chlorination reaction. Then, while maintaining the temperature at 10°±1° C., chlorine gas of a total amount of 8.0 mol was introduced at a rate of 200 to 250 ml/min. At this time, a generated hydrogen chloride gas was absorbed in an aqueous solution of sodium hydroxide.

The chlorinated solution obtained by the chlorination reaction was submitted to vacuum distillation to remove low-boiling point components such as unreacted butyraldehyde and the like, thus obtaining 825 g of a chlorinated solution containing CBA as a major component. This chlorinated solution was subjected to azeotropic distillation while adding 1,050 g of benzene at a rate of 30 g/min to obtain 1,310 g of a distillate which distilled at 90° to 96° C. This distillate was confirmed to contain 30.6% of CBA and 66.5% of benzene by gas chromatography. The yield of distilled CBA based on the CBA contained in the chlorinated solution used was 87.5%.

(Synthesis of Trimer)

Using the same equipment as used in Example 4, 1,000 g of the distillate obtained by the azeotropic distillation was trimerized with the addition of 350 g of H-mordenite (HSZ-620HOA: trademark, manufactured by Tosoh Co., Ltd.) at 30° C. for 3 days while stirring. After the completion of the reaction, H-mordenite catalyst was removed by filtration and the filtrate was distilled under vacuum to evaporate benzene and unreacted aldehyde, thus obtaining 186 g of a colorless, viscous fraction having a boiling point range of 145° to 147° C. at 0.4 kPa. This fraction was CBA trimer with a purity of 99.4%, which began to gradually crystallize at a temperature below 15° C.

The yield of the CBA trimer based on the CBA contained in the distillate used for the trimerization reaction was 60.4%.

Benzene and CBA not trimerized, which were recovered by the vacuum distillation, could be recycled for reuse.

Example 7

Synthesis of MCA Trimer

A trimerization reaction of MCA was carried out using 1,000 g of a distillate obtained by the chlorination of para-aldehyde and the azeotropic distillation in the same manner as in Example 4.

The procedure of Example 4 was followed for the trimerization reaction, except that stannous chloride was used instead of the zinc chloride catalyst of Example 4.

The yield of MCA trimer based on the MCA contained in the distillate used for the trimerization reaction was 76%.

Examples 8, 9

Synthesis of MCA Trimer

Trimerization reactions of MCA were carried out using 1,000 g of a distillate obtained by the chlorination of para-aldehyde and the azeotropic distillation in the same manner as in Example 4.

The procedure of Example 5 was followed for the trimerization reactions, except that HY-zeolite (HSZ-320HOA: trademark, manufactured by Tosoh Co., Ltd.) and L-zeolite were used instead of the H-mordenite of Example 5.

The yields of MCA trimer based on the MCA contained in the distillate used for the trimerization reaction are given in Table 1.

TABLE 1

| Example | Catalyst | Yield |
|---------|-----------|-------|
| 8 | HY-zeolite | 56% |
| 9 | L-zeolite | 67% |

As illustrated above, according to the process of the present invention, not only the catalysts used in the trimerization reactions of 2-chloroaldehydes can be easily separated from the reaction products, but also a high yield of the trimers can be achieved. In addition, the unreacted aldehyde can be easily recovered and efficiently used.

Obviously, numerous modifications and variations of the present invention are possible in light of the above teachings. It is therefore to be understood that within the scope of the appended claims, the invention may be practiced otherwise than as specifically described herein.

What is claimed is:

1. A process for manufacturing a trimer of an aliphatic aldehyde with chlorinated 2-position represented by the following formula,

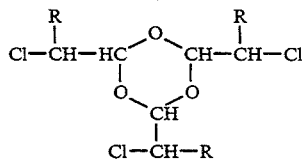

wherein R represents a hydrogen atom, a methyl group, an ethyl group, or a propyl group, which comprises cyclically trimerizing an aliphatic aldehyde having 2 to 5 carbon atoms with chlorinated 2-position in the presence of a catalyst selected from the group consisting of metallic tin, metallic zinc, zeolite, and Lewis acids.

2. The process according to claim 1, wherein said cyclic trimerization reaction is carried out in an organic solvent.

3. A process for manufacturing a trimer of a lower aliphatic aldehyde with chlorinated 2-position comprising, a step of chlorinating an aliphatic aldehyde having 2 to 5 carbon atoms to produce a chlorinated solution containing the aliphatic aldehyde with chlorinated 2-position, a step of distilling said chlorinated solution to remove unreacted aldehyde and high boiling point components, a step of cyclically trimerizing said aliphatic aldehyde with chlorinated 2-position by the addition of a catalyst selected from the group consisting of metallic tin, metallic zinc, zeolite, and Lewis acids, and a step of separating said catalyst and all or a major portion of the organic solvent from the reaction mixture obtained by the cycle trimerization reaction and separating the trimer of the aliphatic aldehyde with chlorinated 2-position as crystals.

4. The process according to claim 1, wherein said metallic tin or metallic zinc is in the form of particles.

5. The process according to claim 1, wherein said zeolite is mordenite, HY-type zeolite or L-type zeolite.

6. The process according to claim 1, wherein said Lewis acid is stannous chloride, zinc chloride, or antimony trichloride.

7. The process according to claim 3, wherein said distillation is azeotropic distillation.

8. The process according to claim 3, wherein said metallic tin or metallic zinc is in the form of particles.

9. The process according to claim 3, wherein said zeolite comprises at least one member selected from the group consisting of mordenite, HY-type zeolite or L-type zeolite.

10. The process according to claim 3, wherein said Lewis acid comprises at least one member selected from the group consisting of stannous chloride, zinc chloride, or antimony trichloride.

* * * * *